United States Patent [19]

Rich et al.

[11] Patent Number: 4,754,639
[45] Date of Patent: Jul. 5, 1988

[54] DEVICE FOR TESTING SUSPENSIONS

[75] Inventors: Kirk K. Rich, Roseville; Robert E. Wold, Royal Oak, both of Mich.

[73] Assignee: Johnstone Pump Company, Troy, Mich.

[21] Appl. No.: 926,259

[22] Filed: Nov. 3, 1986

[51] Int. Cl.⁴ ............................................. G01N 11/00
[52] U.S. Cl. ....................................... 73/53; 73/61 R; 210/90
[58] Field of Search .............. 73/53, 61.4, 61 R, 32 R, 73/863.21; 92/181 R, 172; 210/90, 416.1, 92.1

[56] References Cited

U.S. PATENT DOCUMENTS

| | | |
|---|---|---|
| 2,990,238 | 6/1961 | Kabisch et al. ................... 210/416.1 |
| 3,150,571 | 9/1964 | Frassetto et al. ................... 92/181 R |
| 4,224,821 | 9/1980 | Taylor et al. ....................... 210/96.1 |
| 4,329,869 | 5/1982 | Toda ..................................... 73/61 R |
| 4,413,059 | 11/1983 | Tihon et al. ....................... 210/416.1 |

FOREIGN PATENT DOCUMENTS 22936 2/1983 Japan ....................................... 73/76

OTHER PUBLICATIONS

Research Disclosure, May 1978.

Primary Examiner—Stewart J. Levy
Assistant Examiner—Hezron E. Williams
Attorney, Agent, or Firm—Krass & Young

[57] ABSTRACT

Apparatus for evaluating physical properties of suspensions, particularly the tendency of the solid and fluid portions of a suspension to separate under pressure. The apparatus comprises a pressure vessel having an input port, a bleeder port and a pressure measuring port. A piston is slideably mounted within the pressure vessel and has a head portion which is exposed through a retainer ring for contact by the force applying apparatus. Depending upon the design of the piston, the apparatus may be used either for the separation test described above or for a density evaluation test.

18 Claims, 2 Drawing Sheets

DEVICE FOR TESTING SUSPENSIONS

INTRODUCTION

This invention pertains to test devices and particularly to a device for determining certain physical properties of suspensions such as sealants by applying pressure to a small quantity or the suspension.

BACKGROUND OF THE INVENTION

The assembly of, for example, an automobile involves the application of numerous viscous suspensions such as adhesives, sealants and sound-deadening materials. These suspensions are typically pumped under pressure from a large supply through flexible lines extending from the supply to a point of application and are applied through guns having operator controlled valves to permit controlled applications.

Many suspensions, consisting of both solid particulates and fluid components such as solvents and plasticizers, are known to separate under pressure. If such a phenomenon occurs within the dispensing system, the solid component or components may cake and plug the pump or the lines to the dispensing gun. In a fast moving assembly operation, typical of automotive mass production, the separation of the suspension in the dispensing apparatus may either result in the delivery and application of an improperly balanced mixture or, at worst, may require the dispensing system to be dismantled and cleared by flushing. Production, therefore, is either slowed down or stopped while corrections are made.

SUMMARY OF THE INVENTION

The present invention is an apparatus which permits the testing of industrial suspensions prior to the charging of a dispensing system with such a suspension thereby to determine in advance whether or not the suspension is likely to cause problems of the type described above when the dispensing system is put into full operation.

More specifically, the invention provides a simple and economical apparatus for evaluating the propensity of a suspension to separate under pressure. In addition, a modified form of the invention may be used to determine the density of a suspension.

Broadly defined, the invention comprises a hollow pressure vessel preferably, but not necessarily, defined by a cylindrical body of a rigid material having a bottom and a hollow interior defining a chamber for a slideable piston. A first port is formed in the bottom of the vessel for admitting a charge of the suspension to the chamber and a plug is provided for sealing the port after the suspension charge is admitted. A second port formed in the body between the opposite ends thereof provides for bleeding air and, as hereinafter described in detail, a small quantity of the charge from the chamber. The second port is thereafter sealed by means of a suitable plug. The third port in the body is connected to a pressure gage so that pressure applied to the charge can be regulated. Finally, the apparatus comprises a container mounted on the top of the vessel to retain the piston within the chamber and having an opening which admits a component of a press so that force can be applied to the top of the piston tending to compress the suspension within the vessel.

In the form utilized to evaluate the tendency of the suspension to separate and cake, the piston is formed in such a way as to permit the separated fluid component of the suspension to pass through a small channel to the atmosphere whereas the solid material is retained under pressure within the chamber.

In the density measuring embodiment, the piston is unported; i.e. solid, and permits neither component of the suspension to pass from the pressure chamber.

In both forms, the final operative combination comprises a press which is constructed to receive the pressure vessel in the fully assembled and charged condition and to directly apply a force to the piston in a direction tending to compress the suspension until the desired pressure condition is achieved.

DETAILED DESCRIPTION OF THE ILLUSTRATIVE EMBODIMENTS

Figure 1:
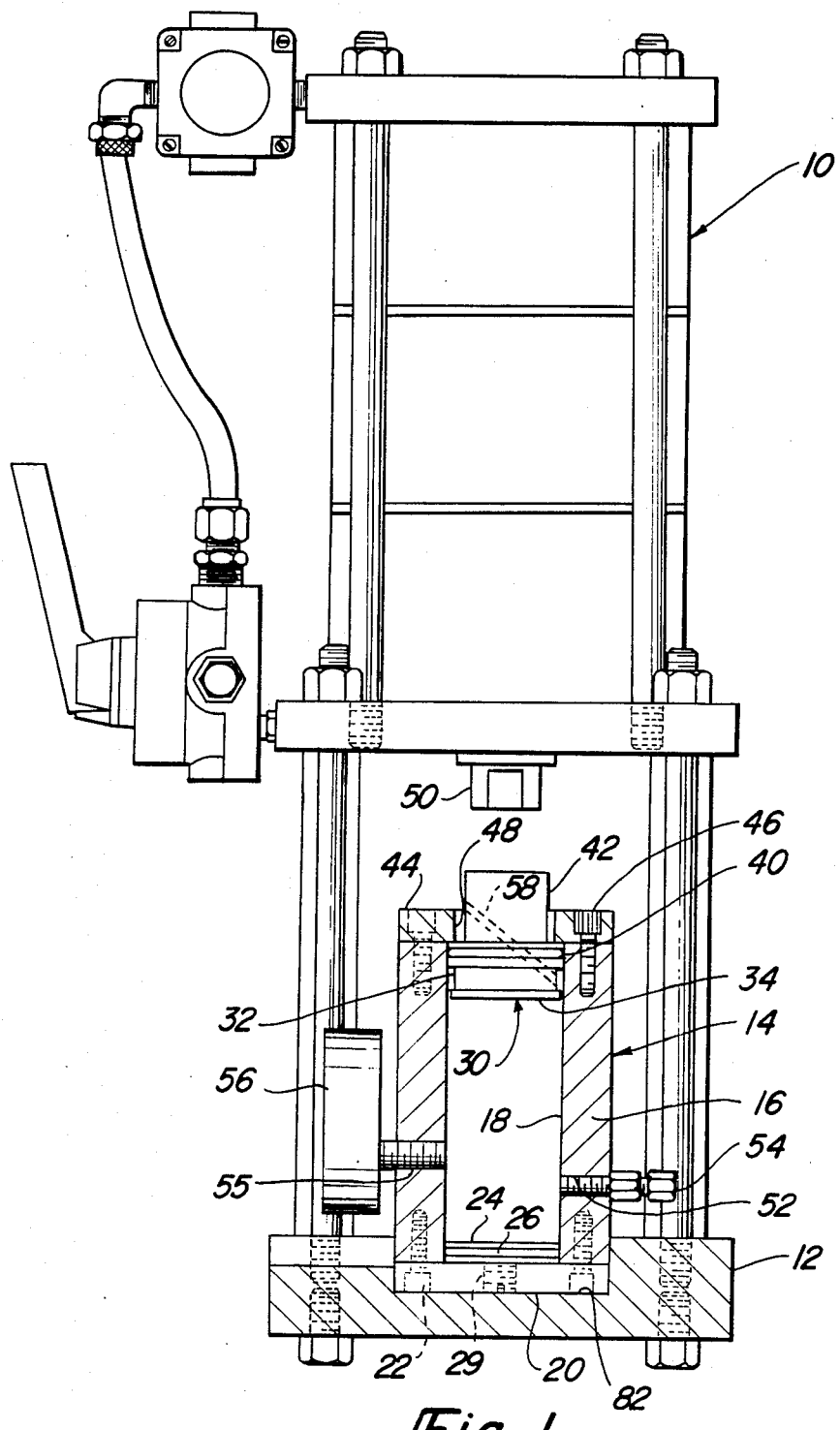
FIG. 1 is a front view, partly in section, of a press and a pressure vessel for testing suspensions.
Figure 2:
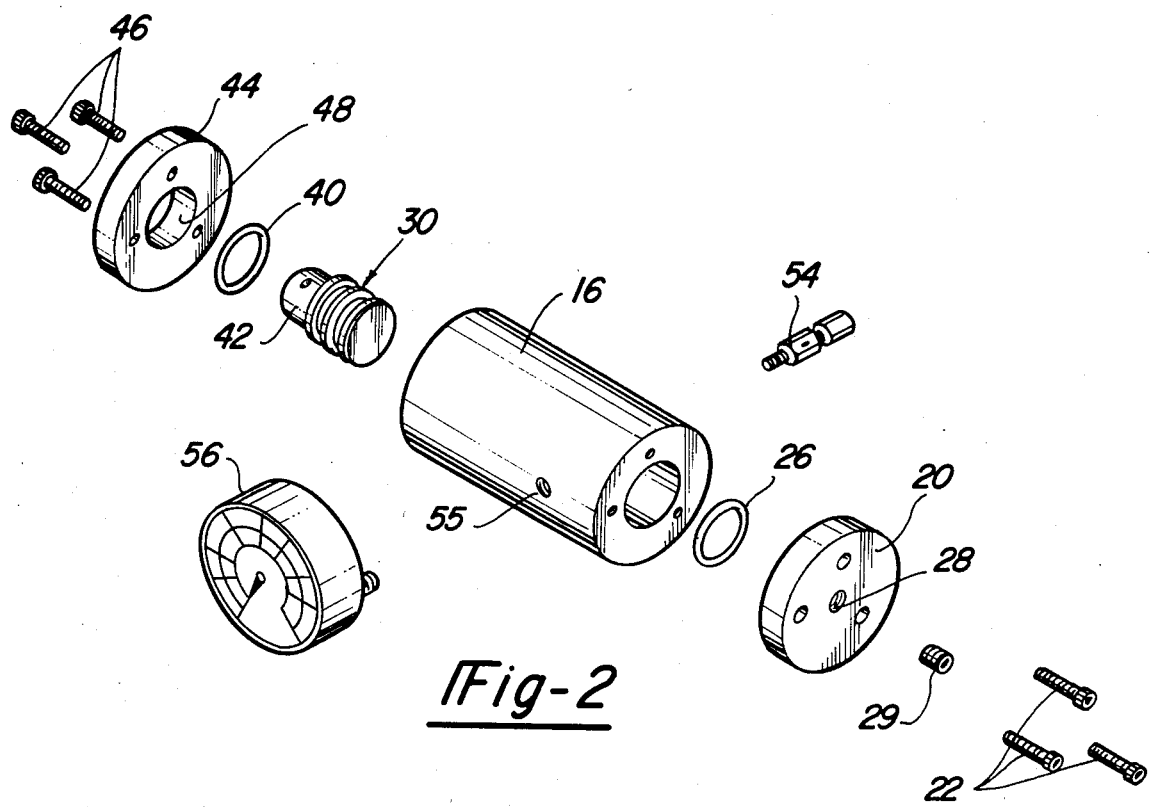
FIG. 2 is an exploded view of the pressure vessel.
Figure 3:
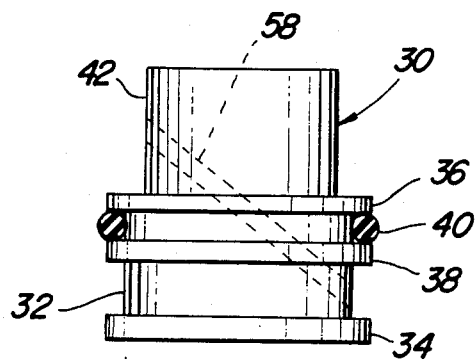
FIG. 3 is a detail view of the piston in the separation tester embodiment.

Referring to the drawing, the suspension test apparatus is shown to comprise a pneumatic press 10 having a base 12 for receiving a pressure vessel 14, the press 10 being multi-stage and operative to apply controlled pressure to a quantity or charge of suspension held within the pressure vessel 14.

The pressure vessel 14 comprises a cylindrical body 16 of heavy rigid material such as steel having a cylindrical internal bore 18 to define a chamber as hereinafter described. The cylindrical form of the body 16 is not essential but, as will be apparent to those skilled in the art, is preferred for ease of manufacture using conventional turning machinery. A bottom cap 20 of steel conforming to the outer diameter of the body 16 is held tightly to the body 16 by means of machine screws 22 in suitably formed and tapped holes. A flange 24 on the interior surface of the bottom cap 20 extends into the bore 18 of the body 16 and retains an O-ring seal 26 which bears against the bore 18 so that the entire vessel 14 may be sealed for pressurization as hereinafter described.

A port 28 is formed in the bottom cap 20 centrally and axially and is threaded to receive a plug 29 to seal the bottom cap 20 after a charge of the tested suspension is admitted to the chamber defined by bore 18 through the port 28.

Fitted within the bore 18 of the body 16 is a steel piston 30 which is also cylindrical and adapted to slide axially within the bore 18 between a bottom position (not shown) and a top position (shown). Piston 30 exhibits a cylindrical body portion 32 which is smaller in diameter than the internal diameter of the bore 18 and a contiguous bottom flange 34 of cylindrical configuration. In the embodiment of FIG. 1, which is used for separation testing, flange 34 is formed to provide a radial clearance of 0.001 inch with the bore 18 for reasons hereinafter described. Additional axially spaced flanges 36 and 38 trap an O-ring seal 40. A head 42 extends axially above the body portion 32 and is smaller in diameter than both the body portions 32 and the flanges 35,38.

The pressure vessel 14 further comprises a retainer cap 44 formed to conform in the outer diameter of the body 16 and held to the top of the body 16 by means of machine screws 46. Cap 44 exhibits a central opening 48 of a diameter which is substantially larger than the diameter of the head 42 of the piston 30 thereby to permit the head 42 to extend through and outwardly of the retainer cap 44 when the piston is in the topmost position shown. This permits the ram 50 of the press 10 to contact the top of the head 42 of the piston 30 thereby to apply a downward force to the piston 30 and a pressure to the charge within the bore 18 of the pressure vessel 14.

In the separation test embodiment, the piston 30 is further provided with a channel 58 having an inlet opening in the side of the body portion 32 and extending diagonally upwardly to the side wall of the head 42 which is external of the pressure chamber.

Body 16 of pressure vessel 14 is bored through the side wall at a point spaced above the bottom a distance greater than the axial distance between the bottom of flange 34 and the top of flange 38 of the piston 30 to provide a bleeder port 52. A plug 54 is provided for sealing the bleeder port after it has performed its function as hereinafter described. Finally, the side wall of body 16 is bored through to provide a port 55 to which a conventional pressure gage 56 is connected.

Base 12 of press 10 is machined to provide a shallow cylindrical depression 82 which receives vessel 14.

The operation of the apparatus thus far described in the separation testing mode is as follows. The pressure vessel 14 is assembled as shown in FIG. 1 with the bottom plate 20 in place, the plug 29 removed, the plug 54 of the bleeder port removed and the gage 56 in place. The piston 30 is bottomed so that flange 34 is either against or immediately adjacent the flange 24.

The suspension to be tested is pumped by means of a dispenser gun through the port 28 causing the piston 30 to move axially toward the top position, eventually opening the port 52 so that any trapped air and, preferably, a small quantity of the suspension material passes through the port. At this point plug 54 is installed and additional material is pumped into the chamber defined by bore 18 until the piston 30 reaches the topmost position. The dispenser gun is disconnected and the plug 29 is installed.

The pressure vessel 14 is placed in the cylindrical depression of the base 12 of the press 10 as shown in FIG. 1, and the press is actuated to bring the ram 50 into engagement with the head 42 of piston 30. The press 10 is further actuated to drive the piston 30 downwardly thereby to compress the charge until the desired pressure condition is reached. This condition is typically maintained for a space of, for example, 24 hours.

In the suspension separation testing mode, the small 0.001 inch radial clearance between the flange 34 and the interior bore 18 of body 16 permits plasticizers and solvents to pass around the flange 34 and travel through the channel 58 to the atmosphere. Solid particulate matter, however, cannot pass through this small clearance and is trapped under compression and under pressure as applied by the piston 30 within the chamber defined be bore 18. The result of the test is evaluated visually by disassembly and inspection after the desired time period.

Figure 4:
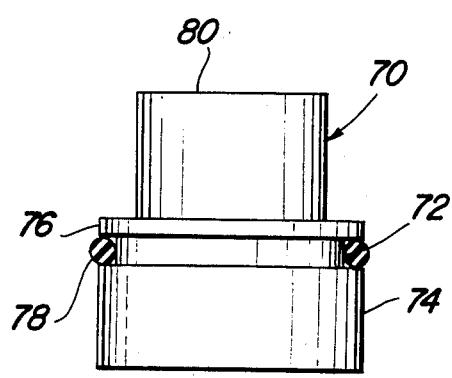
FIG. 4 is a detail of the piston in the density tester embodiment.

Referring now to FIG. 4, an alternative form of the piston is shown for use in density measurement. The alternative piston 70 comprises a steel body having a nominal cylindrical diameter 72, a larger diameter solid base 74 and a top flange 76 which traps an O-ring seal 78 between itself and the base 74. A head portion 80 corresponding to the head 42 of piston 30 is also provided. There is no counterpart to the channel 58 and the base portion 74 is of sufficient diameter as to fit snuggly and sealingly against the interior wall of the through bore 18.

The density test procedure is exactly as defined above with the exception that the charge of material is weighed and measured for volume to provide reference data. The desired pressure is applied for the desired time via press 10 and piston 70. However, contrary to the previous embodiment, no material is allowed to separate out of and pass from the pressure chamber.

After the desired period of compression, the charge is again weighed and measured for volume. The reduction of volume is a measure of density.

By way of example, the pressure vessel 14 may be 5.0 inches long and 3.47 inches in outside diameter. The diameter of bore 18 is 1.75 inches. Gauge 56 reads to 4000 psi.

We claim:

1. Apparatus for determining physical properties of suspensions having both solid and fluid components comprising:
   a rigid body having a bottom and a hollow interior defining an axial slide chamber for a piston;
   a piston slidably disposed within the chamber and displaceable between a bottom position at one end of the chamber and a top position at the opposite end of the chamber;
   a first port in the bottom for admitting a charge of the suspension to the chamber;
   a first plug for sealing the first port after the suspension charge is admitted;
   a second port in the body between ends for bleeding air from the chamber as it is charged;
   a second plug for sealing the second port;
   a third port in the body;
   a pressure gage connected to the third port for determining the pressure applied to the charge; and
   a retainer mounted on the top of the body to retain the piston in the chamber but having an opening to admit a component of a press for applying a force to the piston to compress the charge.

2. Apparatus as defined in claim 1 wherein the chamber and the piston are cylindrical.

3. Apparatus as defined in claim 1 wherein the piston has formed therein a channel for allowing the fluid component to exit the chamber when the charge is pressurized.

4. Apparatus for determining physical properties of suspensions having both solid and fluid components comprising:
   a rigid body having a bottom and a hollow interior defining an axial slide chamber for a piston;
   a piston slidably disposed within the chamber and displaceable between a bottom position as one end of the chamber and a top position at the opposite end of the chamber;
   a first port in the bottom for admitting a charge of the suspension to the chamber;
   a first plug for sealing the first port after the suspension change is admitted;
   a second port in the body between ends for bleeding air from the chamber as it is charged;
   a second plug for sealing the second port;
   a third port in the body;

a pressure gage connected to the third port for determining the pressure applied to the charge; and a retainer mounted on the top of the body to retain the piston in the chamber but having an opening to admit a component of a press for applying a force to the piston to compress the charge, and piston comprising a solid, essentially cylindrical body having a lower cylindrical flange of larger dimater than the body which fits within the chamber with a small radial clearance to allow the fluid component of the charge to pass through the clearance, and a seal spaced axially above the flange; said channel having an input port in the cylindrical element between the flange and the seal.

5. Apparatus as defined in claim 4 wherein the piston further comprises an upper flange of larger diameter than the body and the opening in the retainer to trap the piston in the chamber.

6. Apparatus as defined in claim 5 wherein the piston further comprises a head portion which projects through the retainer opening when the piston is in the top position.

7. Apparatus as defined in claim 1 wherein the piston is solid and fully seals the charge when bearing thereagainst to compress both solid and fluid components thereof.

8. Apparatus as defined in claim 1 wherein the bottom is formed as a separate component from the hollow slide chamber body.

9. Apparatus for determining the physical properties of suspensions having both solid and fluid components comprising:

a rigid body having a bottom, a hollow interior bore defining a pressure chamber;

a piston slidably disposed within the chamber and displaceable between a bottom position at one end of the chamber and a top position at the other end of the chamber;

a first port in the bottom for admitting a charge of the suspension; a plug for said first port;

a second port in the body between the ends for bleeding air from the chamber as it is filled; a plug for said second port;

pressure sensing means connected through said body to the chamber;

a retainer mounted on the top of the body to retain the piston in the chamber but having an opening to allow a component of a press for applying a force to the piston to compress the charge; and press means independent of said body but adapted to receive said body in an unattached support position said press having a component contacting said piston through said opening to apply a force thereto.

10. Apparatus as defined in claim 9 wherein the chamber and the piston are cylindrical.

11. Apparatus as defined in claim 9 wherein the piston has formed therein a channel for allowing the fluid component to exit the chamber when the charge is pressurized.

12. Apparatus as defined in claim 9 wherein the piston comprises a solid, essentially cylindrical body having a lower cylindrical flange of larger diameter than the body which fits within the chamber with a small radial clearance to allow the fluid component of the charge to pass through the clearance, and a seal spaced axially above the flange; said channel having an input port in the cylindrical element between th flange and the seal.

13. Apparatus as defined in claim 12 wherein the piston further comprises an upper flange of larger diameter than the body and the opening in the retainer to trap the piston in the chamber.

14. Apparatus as defined in claim 13 wherein the piston further comprises a head portion which projects through the retainer opening when the piston is in the top position.

15. Apparatus as defined in claim 9 wherein the piston is solid and fully seals the charge when bearing thereagainst to compress both solid and fluid components thereof.

16. Apparatus as defined in claim 9 wherein the bottom is formed as a separate component from the hollow slide chamber body.

17. Apparatus as defined in claim 9 wherein said press further comprises a base having a depression to receive an secure said body in a manner such that said body may be removed from said depression after said component of said press means has applied the force to said piston.

18. Apparatus as defined in claim 17 wherein said depression is substantially cylindrical.

* * * * *